United States Patent
Wang et al.

(10) Patent No.: US 9,416,074 B2
(45) Date of Patent: *Aug. 16, 2016

(54) PROCESS FOR PRODUCING 2,3,3,3-TETRAFLUOROPROPENE

(71) Applicant: HONEYWELL INTERNATIONAL INC., Morristown, NJ (US)

(72) Inventors: Haiyou Wang, Amherst, NY (US); Hsueh Sung Tung, Getzville, NY (US); Daniel C. Merkel, West Seneca, NY (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/351,688

(22) PCT Filed: Oct. 10, 2012

(86) PCT No.: PCT/US2012/059437
§ 371 (c)(1),
(2) Date: Apr. 14, 2014

(87) PCT Pub. No.: WO2013/055722
PCT Pub. Date: Apr. 18, 2013

(65) Prior Publication Data
US 2014/0350309 A1    Nov. 27, 2014

Related U.S. Application Data

(63) Continuation-in-part of application No. 13/287,199, filed on Nov. 2, 2011, now Pat. No. 8,455,704, which is a continuation-in-part of application No. 12/167,159, filed on Jul. 2, 2008, now Pat. No. 9,040,759.

(60) Provisional application No. 61/547,219, filed on Oct. 14, 2011, provisional application No. 60/958,468, filed on Jul. 6, 2007.

(51) Int. Cl.
C07C 17/00     (2006.01)
C07C 17/38     (2006.01)
C07C 17/25     (2006.01)
C07C 17/087    (2006.01)
C07C 17/20     (2006.01)

(52) U.S. Cl.
CPC .............. *C07C 17/25* (2013.01); *C07C 17/087* (2013.01); *C07C 17/202* (2013.01)

(58) Field of Classification Search
CPC ........ C07C 17/087; C07C 17/23; C07C 17/25; C07C 21/18
USPC .......................................... 570/155, 156, 177
See application file for complete search history.

(56) References Cited

U.S. PATENT DOCUMENTS

| | | | |
|---|---|---|---|
| 2,931,840 | A | 8/1960 | Marquis |
| 4,900,874 | A | 2/1990 | Ihara et al. |
| 5,155,082 | A | 10/1992 | Tung et al. |
| 5,162,594 | A | 11/1992 | Krespan |
| 7,884,254 | B2 | 2/2011 | Wang et al. |
| 8,252,954 | B2 | 8/2012 | Raston et al. |
| 2007/0197842 | A1 | 8/2007 | Mukhopadhyay et al. |
| 2009/0043136 | A1 | 2/2009 | Wang et al. |
| 2009/0043137 | A1 | 2/2009 | Wang et al. |
| 2009/0240090 | A1 | 9/2009 | Merkel et al. |
| 2010/0029997 | A1 | 2/2010 | Wang et al. |
| 2010/0036179 | A1 | 2/2010 | Merkel et al. |
| 2010/0331583 | A1 | 12/2010 | Johnson et al. |
| 2011/0031436 | A1 | 2/2011 | Mahler et al. |
| 2011/0160498 | A1 | 6/2011 | Pigamo et al. |
| 2012/0053371 | A1 | 3/2012 | Johnson et al. |

FOREIGN PATENT DOCUMENTS

| | | |
|---|---|---|
| CN | 101535227 A | 9/2009 |
| CN | 101597209 A | 12/2009 |
| CN | 102099319 A | 6/2011 |
| EP | 2 149 543 A1 | 2/2010 |
| WO | 2011/087825 A1 | 7/2011 |

OTHER PUBLICATIONS

Banks, R. E., et al., "Preparation of 2,3,3,3-tetrafluoropropene from trifluoroacetylacetone and sulphur tetrafluoride", Journal of Fluorine Chemistry 82:171-174 (1997).
Supplementary European Search Report corresponding to RP 12 84 0366, dated Apr. 23, 2015.

*Primary Examiner* — Jafar Parsa
(74) *Attorney, Agent, or Firm* — Scully, Scott, Murphy & Presser, P.C.

(57) ABSTRACT

The present invention relates, in part, to the discovery that the presence of impurities in a reactor for dehydrochlorinating HCFC-244bb to HFO-1234yf results in a reduced conversion rate and/or a selectivity changeover from HFO-1234yf to HCFO-1233xf. By substantially removing such impurities, it is shown that the conversion rate may be improved and selectivity to HFO-1234yf via dehydrochlorination of HCFC-244bb is also improved.

17 Claims, 2 Drawing Sheets

PROCESS FOR PRODUCING 2,3,3,3-TETRAFLUOROPROPENE

CROSS REFERENCES TO RELATED APPLICATIONS

This application claims priority to U.S. Provisional Application No. 61/547,219, filed Oct. 14, 2011, the contents of which are incorporated herein by reference.

This application is also a continuation-in-part of U.S. application Ser. No. 13/287,199, filed on Nov. 11, 2011, the contents of which are incorporated herein by reference.

This application is also is a continuation-in-part of U.S. application Ser. No. 12/167,159, filed Jul. 2, 2008, which claims priority to U.S. Provisional Application No. 60/958,468, filed Jul. 6, 2007, the contents each of which are incorporated herein by reference.

FIELD OF INVENTION

This invention relates to a process for preparing fluorinated organic compounds, more particularly to a process for preparing fluorinated olefins, and even more particularly to a process for producing 2,3,3,3-tetrafluoropropene (HFO-1234yf).

BACKGROUND OF THE INVENTION

Hydrofluoroolefins (HFOs), such as tetrafluoropropenes (including 2,3,3,3-tetrafluoropropene (HFO-1234yf)), are now known to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFOs do not contain chlorine and, thus, pose no threat to the ozone layer. HFO-1234yf has also been shown to be a low global warming compound with low toxicity and, hence, can meet increasingly stringent requirements for refrigerants in mobile air conditioning. Accordingly, compositions containing HFO-1234yf are among the materials being developed for use in many of the aforementioned applications.

Several methods of preparing HFOs are known. For example, U.S. Pat. No. 4,900,874 (Ihara et al.) describes a method of making fluorine containing olefins by contacting hydrogen gas with fluorinated alcohols. Although this appears to be a relatively high-yield process, commercial scale handling of hydrogen gas at high temperature is hazardous. Also, the cost of commercially producing hydrogen gas, such as building an on-site hydrogen plant, is economically costly.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted to unwanted and/or unimportant byproducts, including a sizeable amount of carbon black which tends to deactivate the catalyst used in the process.

The preparation of HFO-1234yf from trifluoroacetylacetone and sulfur tetrafluoride has been described (See Banks, et al., Journal of Fluorine Chemistry, Vol. 82, Iss. 2, p. 171-174 (1997)). Also, U.S. Pat. No. 5,162,594 (Krespan) discloses a process wherein tetrafluoroethylene is reacted with another fluorinated ethylene in the liquid phase to produce a polyfluoroolefin product.

However, there remains a need for an economic means of producing hydrofluoroolefins, such as HFO-1234yf. The present invention satisfies this need among others.

SUMMARY OF THE INVENTION

The present invention relates, in part, to the surprising discovery that, during the dehydrochlorination of 2-chloro-1,1,1,2-tetrafluoropropane (HCFC-244bb) to HFO-1234yf in a reactor, impurities formed through halidation of the materials of the reactor leads to a reduction of the HFO-1234yf production rate and/or selectivity changeover from HFO-1234yf to 2-chloro-3,3,3-trifluoropropene (HCFO-1233xf). Accordingly, the present invention relates to methods of improving HFO-1234yf production and selectivity by reducing the presence of impurities in the reactor and avoiding, or at least reducing, the formation of HCFO-1233xf.

In one aspect, the present invention relates to a process for preparing 2,3,3,3-tetrafluoropropene comprising (a) removing impurities from a reactor such that the reactor is substantially free of impurities, (b) providing a starting composition comprising HCFC-244bb in the reactor, and (c) contacting the starting composition in the reactor with a dehydrochlorination catalyst to produce a final composition comprising HFO-1234yf. As used herein, the definition of "substantially free" means that the amount of impurities is reduced in the reactor so as to measurably improve the HFO-1234yf production rate and/or selectivity of the conversion of HCFC-244bb to HFO-1234yf. It may also mean the decrease in the conversion of HCFC-244bb to HCFO-1233xf. The impurities may include, but are not limited to, metal halides, metal oxides, and/or carbonaceous materials. The metal halides can comprise, for example, halides of Ni, Cr, Fe, Mo, Nb, Cu, and Co.

In certain embodiments, the step of removing impurities from the reactor comprises introducing a reducing agent into the reactor under conditions effective to convert any metal halides or metal oxides into metallic metals. Such reducing agents may include, but are not limited to, $H_2$, $NH_3$, CO, $C_1$-$C_{12}$ hydrocarbons, and combinations of these. The reducing agent can be in pure or in diluted form, e.g. diluted with inert gases. The dilution can be as high as practically possible, for example about 0.1% volume of reducing agent. This step may be performed alone or in conjunction with any other step for removing impurities. In certain embodiments, reducing occurs under conditions of continuous flow of reducing agent. In one embodiment, the reactor thus subjected to reducing can be afterward kept under positive pressure, or be sealed, with reducing agent and/or inert gas.

In alternative embodiments, the step of removing impurities from the reactor comprises introducing an oxidizing agent into the reactor under conditions effective to burn off the carbonaceous materials in the reactor. The oxidizing agent, for example, can comprise, but are not limited to, $H_2O$, $CO_2$, $O_2$ (oxygen), air, $O_3$, $Cl_2$, $N_2O$, and combinations of these. This step may be performed alone or in conjunction with any other step for removing impurities. In one embodiment, oxidizing occurs under conditions of continuous flow of oxidizing agent. In another embodiment, the oxidizing agent is diluted or provided in diluted form. Suitable diluents include inert gases, including, for example, He, Ar, $N_2$, and combinations of these. In one practice of this embodiment, the oxidizing agent is oxygen present in air and is diluted with nitrogen. The dilution can be as high as practically possible, for example about 0.1% volume of oxidizing agent.

In certain embodiments, introduction of an oxidizing agent is performed immediately preceding the introduction of the reducing agent; in certain embodiments of this practice, there is an interceding purge step between the oxidation and reduction. In certain embodiments, the purge step involves introducing inert gas into the reactor, inert gases including, for example, He, Ar, $N_2$, and combinations of these. In certain embodiments, the reactor is purged with the inert gas at a temperature of from about 100° C. to about 700° C., about 200° C. to about 600° C., about 300° C. to about 500° C., or about 400° C. to about 500° C. In one embodiment, purging is performed under conditions of continuous flow of inert gas. In another embodiment, the reactor is pressurized with inert gas and then depressurized for a few times sufficient to accomplish purging. Combinations of these embodiments may also be implemented.

In further alternative embodiments, the step of removing impurities from the reactor comprises physically removing carbonaceous materials and metal halides from the reactor. The physical removal can be achieved by, for example, electrical polishing and/or mechanical polishing of the interior surface of the reactor. In another example, these impurity deposits can be washed away with high flow rate of water or steam. This step may be performed alone or in conjunction with any other step for removing impurities.

In certain embodiments, the step of contacting the starting composition with a dehydrochlorination catalyst occurs in the vapor phase. The catalyst, for example, may be selected from the group consisting of (i) one or more halides, (ii) one or more halogenated metal oxides, (iii) one or more zero-valent metals/metal alloys, and (iv) a combination of two or more of these. In certain embodiments, the selectivity to HFO-1234yf is at least 90% or higher, 95% or higher, or 97% or higher.

In another aspect, the present invention relates to a process for preparing HFO-1234yf by (a) providing a starting composition comprising 2-chloro-1,1,1,2-tetrafluoropropane in a reactor that is substantially free of impurities, and (b) contacting the starting composition in the reactor with a dehydrochlorination catalyst to produce a final composition comprising 2,3,3,3-tetrafluoropropene. In certain embodiments, the selectivity to HFO-1234yf is at least 90% or higher, 95% or higher, or 97% or higher.

In even further aspects, the present invention relates to a process for preparing HFO-1234yf by
  (i) providing a starting composition including a compound of Formulas I, II, or III:

$$CX_2=CCl-CH_2X \quad (I);$$

$$CX_3-CCl=CH_2 \quad (II); or$$

$$CX_3-CHCl-CH_2X \quad (III)$$

wherein X is independently selected from F, Cl, Br, and I, provided that at least one X is not fluorine;
  (ii) contacting the starting composition with a first fluorinating agent to produce a first intermediate composition including 2-chloro-3,3,3-trifluoropropene;
  (iii) contacting the first intermediate composition with a second fluorinating agent to produce a second intermediate composition including 2-chloro-1,1,1,2-tetrafluoropropane; and
  (iv) dehydrochlorinating at least a portion of the 2-chloro-1,1,1,2-tetrafluoropropane to produce a reaction product including 2,3,3,3-tetrafluoropropene, wherein the dehydrochlorination step is performed in a reactor that is substantially free of impurities.

Additional embodiments and advantages to the present invention will be readily apparent to one of skill in the art, based on the disclosure provided herein.

DETAILED DESCRIPTION OF PREFERRED EMBODIMENTS

Figure 1:
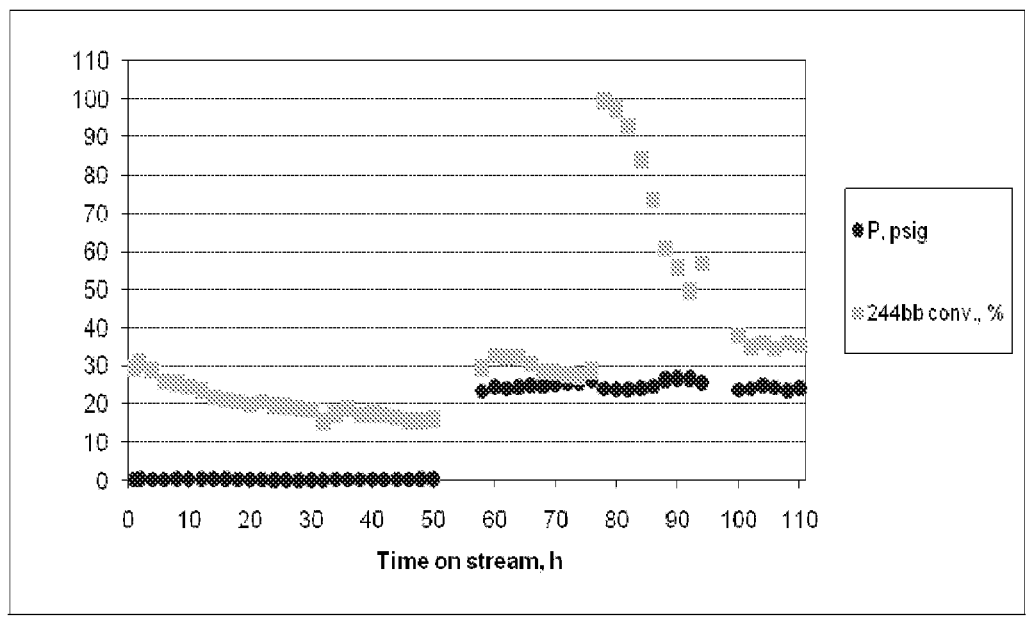
FIG. 1 illustrates conversion of HCFC-244bb conversion and product selectivity.

According to one embodiment, the present invention relates to a manufacturing process for making HFO-1234yf using a starting or intermediate material comprising HCFC-244bb in a reactor that is substantially free of impurities. Applicants have surprisingly found that the presence of impurities, such as metal halides, metal oxides, and carbonaceous materials, decrease the conversion rate and selectivity of HCFC-244bb to HFO-1234yf. While not wishing to be bound by theory, it is believed that certain impurities, such as halides of Ni, Cr, Fe, Mo, Nb, Cu, and Co, are formed through halidation of corresponding metal components of the reactor, and that such impurities catalytically contribute to the formation of HCFO-1233xf. Accordingly, the present invention provides methods of removing impurities from the reactor to improve the overall efficiency of the HFO-1234yf production process.

In certain aspects, the preparation of HFO-1234yf generally includes at least three reaction steps, as follows:
  (i) $(CX_2=CCl-CH_2X$ or $CX_3-CCl=CH_2$ or $CX_3-CHCl-CH_2X)+HF \rightarrow$ 2-chloro-3,3,3-trifluoropropene (HCFO-1233xf)+HCl in a vapor phase reactor charged with a solid catalyst;
  (ii) 2-chloro-3,3,3-trifluoropropene (HCFO-1233xf)+HF$\rightarrow$2-chloro-1,1,1,2-tetrafluoropropane (HCFC-244bb) in a liquid phase reactor charged with a liquid hydrofluorination catalyst; and
  (iii) 2-chloro-1,1,1,2-tetrafluoropropane (HCFC-244bb) $\rightarrow$2,3,3,3-tetrafluoropropene (HFO-1234yf) in a vapor phase reactor.
wherein X is independently selected from F, Cl, Br, and I, provided that at least one X is not fluorine.

The starting material in the first reaction step is one or more chlorinated compounds according to Formulas I, II, and/or III:

$$CX_2=CCl-CH_2X \quad \text{(Formula I)}$$

$$CX_3-CCl=CH_2 \quad \text{(Formula II)}$$

$$CX_3-CHCl-CH_2X \quad \text{(Formula III)}$$

wherein X is independently selected from F, Cl, Br, and I, provided that at least one X is not fluorine. In certain embodiments, these compounds contain at least one chlorine, a majority of X is chlorine, or all X is chlorine.

In the first step, the starting composition (which, in certain embodiments comprises 1,1,2,3-tetrachloropropene (HCO- 1230xa), 2,3,3,3-tetrachloropropene (HCO-1230xf) and/or 1,1,1,2,3-pentachloropropane (HCC-240db)) reacts with anhydrous HF in a first vapor phase reactor (fluorination reactor) to produce a mixture of at least HCFO-1233xf (2-chloro-3,3,3-trifluoropropene) and HCl. The reaction can be carried out at a temperature of about 200-400° C. and a pressure of about 0-200 psig. The effluent stream exiting the vapor phase reactor may optionally comprise additional components, such as un-reacted HF, un-reacted starting compositions, heavy intermediates, HFC-245cb, or the like.

This reaction may be conducted in any reactor suitable for a vapor phase fluorination reaction. The reactor may be constructed from materials which are resistant to the corrosive effects of hydrogen fluoride and catalyst such as Hastalloy, Inconel, Monel. In case of a vapor phase process, the reactor is filled with a vapor phase fluorination catalyst. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures any of which may be optionally halogenated. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

This first step of the reaction is not necessarily limited to a vapor phase reaction and may also be performed using a liquid phase reaction or a combination of liquid and vapor phases, such as that disclosed in U.S. Published Patent Application No. 20070197842, the contents of which are incorporated herein by reference. It is also contemplated that the reaction can be carried out batch wise, continuous, or a combination of these. For embodiments in which the reaction comprises a liquid phase reaction, the reaction can be catalytic or non-catalytic. Lewis acid catalysts, such as metal-halide catalysts, including antimony halides, tin halides, thallium halides, iron halides, and combinations of two or more of these, may be employed. In certain embodiments, metal chlorides and metal fluorides are employed, including, but not limited to, $SbCl_5$, $SbCl_3$, $SbF_5$, $SnCl_4$, $TiCl_4$, $FeCl_3$ and combinations of two or more of these.

In the second step of the process for forming 2,3,3,3-tetrafluoropropene, HCFO-1233xf is converted to HCFC-244bb. In one embodiment, this step may be performed in the liquid phase in a liquid phase reactor, which may be TFE or PFA-lined. Such a process may be performed in a temperature range of about 70-120° C. and about 50-120 psig.

Any liquid phase fluorination catalyst may be used in the invention. A non-exhaustive list include Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Antimony pentachloride is most preferred.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

This second step of the reaction is not necessarily limited to a liquid phase reaction and may also be performed using a vapor phase reaction or a combination of liquid and vapor phases, such as that disclosed in U.S. Published Patent Application No. 20070197842, the contents of which are incorporated herein by reference. To this end, the HCFO-1233xf containing feed stream is preheated to a temperature of from about 50° C. to about 400° C., and is contacted with a catalyst and fluorinating agent. Catalysts may include standard vapor phase agents used for such a reaction and fluorinating agents may include those generally known in the art, such as, but not limited to, hydrogen fluoride.

In the third step of HFO-1234yf production, HCFC-244bb is fed to a second vapor phase reactor (dehydrochlorination reactor) to be dehydrochlorinated to make the desired product 2,3,3,3-tetrafluoropropene (HFO-1234yf). This reactor contains a catalyst that can catalytically dehydrochlorinate HCFC-244bb to make HFO-1234yf.

The catalysts may be metal halides, halogenated metal oxides, neutral (or zero oxidation state) metal or metal alloy, or activated carbon in bulk or supported form. Metal halide or metal oxide catalysts may include, but are not limited to, mono-, bi-, and tri-valent metal halides, oxides and their mixtures/combinations, and more preferably mono-, and bi-valent metal halides and their mixtures/combinations. Component metals include, but are not limited to, $Cr^{3+}$, $Fe3+$, $Mg^{2+}$, $Ca^{2+}$, $Ni^{2+}$, $zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625. Such catalysts may be provided as discrete supported or unsupported elements and/or as part of the reactor and/or the reactor walls.

Preferred, but non-limiting, catalysts include activated carbon, stainless steel (e.g., SS 316), austenitic nickel-based alloys (e.g., Inconel 625), nickel, fluorinated 10% CsCl/MgO, and 10% CsCl/$MgF_2$. A suitable reaction temperature is about 300-550° C. and a suitable reaction pressure may be between about 0-150 psig. The reactor effluent may be fed to a caustic scrubber or to a distillation column to remove the byproduct of HCl to produce an acid-free organic product which, optionally, may undergo further purification using one or any combination of purification techniques that are known in the art.

The reaction may be carried out at a temperature range of from about 200° C. to about 800° C., from about 300° C. to about 600° C., or from about 400° C. to about 500° C. Suitable reactor pressures range from about 0 psig to about 200 psig, from about 10 psig to about 100 psig, or from about 20 to about 70 psig.

In vapor-phase HCFC-244bb dehydrochlorination, HCFC-244bb feed, which can be formed from HCFO-1233xf hydrofluorination as described in US 20090240090, the contents of which are incorporated herein by reference, is fed continuously to a vaporizer and the vaporized feed to a reactor. Due to incomplete conversion of HCFO-1233xf and its close boiling point to HCFC-244bb as well as the formation of azeotrope or azeotrope-like composition of HCFC-244bb and HCFO-1233xf under certain conditions, the separation of these two compounds is difficult. For this reason, the HCFC-244bb feed generally contains certain amount of HCFO-1233xf. The dehydrochlorination reaction may be carried out under conditions to attain a HCFC-244bb conversion of about 5% or higher, about 20% or higher, or about 30% or higher. The reaction may be carried out at a temperature in the range of from about 200° C. to about 800° C., from about 300° C. to about 600° C., or from about 400° C. to about 500° C.; the reactor pressure may be in the range of from about 0 psig to about 200 psig, from about 10 psig to about 100 psig, or from about 20 to about 70 psig.

In general, the effluent from the dehydrochlorination reactor may be processed to achieve desired degrees of separation and/or other processing. Besides HFO-1234yf produced, the effluent generally contains HCl, unconverted HCFC-244bb, and HCFO-1233xf (which is mainly carried over from the previous step of HCFO-1233xf hydrofluorination). Optionally, HCl is then recovered from the result of the dehydrochlorination reaction. Recovery of HCl is conducted by conventional distillation where it is removed from the distillate. Alternatively, HCl can be recovered or removed by using water or caustic scrubbers. When a water extractor is used HCl is removed as an aqueous solution. When a caustic solution is used, HCl is removed from system as a chloride salt in aqueous solution. After the recovery or removal of HCl, the organic stream may be sent to a distillation column for separation. HFO-1234yf, collected from the overhead of the column, may be sent to another column for further purification, while a fraction of the mixture of HCFO-1233xf and HCFC-244bb, accumulated in the reboiler, may be sent back to the dehydrochlorination reactor for the recycle of HCFC-244bb, and the rest to the HCFO-1233xf hydrofluorination reactor for the recycle of HCFO-1233xf.

Applicants have surprisingly discovered that, during the dehydrochlorination of HCFC-244bb to form HFO-1234yf, the presence of impurities in the reactor decreases the selectivity to HFO-1234yf and increases selectivity toward HCFO-1233xf, which is an undesired byproduct. Applicants have further discovered that the same impurities may also increase catalyst deactivation, thus causing a reduction of the conversion rate. While not intending to be bound by theory, it is believed that metal halides such as $NiX_2$ (X=F, or Cl), $CrX_3$, $FeX_3$, $MoX_3$, $NbX_3$, $CoX_2$, and the like, are incidentally formed by halidation of the metal components of the reactor (e.g., Inconel 625), and carbonaceous materials by the pyrolysis of organic compounds present in the reactor. These metal halides, especially trivalent metal halides, act as dehydrofluorination catalysts converting HCFC-244bb to HCFO-1233xf. In other aspects, the metal halides and/or carbonaceous materials block the catalytically active metallic sites converting HCFC-244bb to HFO-1234yf. The present invention provides a solution to this problem by reducing the content of impurities in the reactor, thereby improving HFO-1234yf selectivity and similarly reducing the formation of HCFO-1233xf.

To this end, the impurities in the reactor are removed such that the reactor is substantially free of impurities. As used herein, the term "impurities" includes any compound or combination of compounds that (1) reduce the selectivity of HCFC-244bb to HFO-1234yf, (2) increase selectivity changeover from HFO-1234yf to HCFO-1233xf, and/or (3) decrease the conversion rate of HCC-244bb to HFO-1234yf. Such impurities may include, but are not limited to, metal halides, metal oxides, and carbonaceous materials. As used herein, the definition of "substantially free" means that the amount of impurities is reduced in the reactor so as to measurably improve selectivity of the conversion of HCFC-244bb to HFO-1234yf, decrease selectivity in the conversion of HCFC-244bb to HCFO-1233xf, and/or increase the conversion rate of HCFC-244bb to HFO-1234yf. While the definition of "substantially free" may be as defined herein, in one aspect, the removal of impurities improves selectivity of HCFC-244bb to HFO-1234yf to at least 90% or higher, 95% or higher, or 97% or higher, or 99% or higher, or 99.5% or higher. Selectivity may be calculated by number of moles of product (HFO-1234yf) formed divided by number of moles of reactant consumed or, otherwise, using standard methods known in the art.

The step of removing impurities from the reactor may be accomplished using any method for removing such impurities, particularly the impurities provided herein. In one embodiment, it may be achieved by introducing a reducing agent into the reactor under conditions effective to convert any metal halides or metal oxides into metallic metals. Such reducing agents may include, but are not limited to, $H_2$, $NH_3$, CO, and combinations of these. This reducing step may be carried out in pure or diluted reducing agent, e.g., hydrogen, at a temperature range of from about 100° C. to about 700° C., about 200° C. to about 600° C., about 300° C. to about 500° C., or about 400° C. to about 500° C. Suitable diluents include inert gases such as $N_2$, Ar, and He. When a diluted reducing agent is used, the dilution can be as high as practically possible, for example, about 0.1% volume of reducing agent. In a preferred embodiment, the concentration of reducing agent after dilution ranges from about 0.5 to about 20 vol %, preferably from about 1 to about 5 vol %, and more preferably from about 2 to about 2.5 vol %.

Another method for removing impurities from the reactor may be achieved by introducing an oxidizing agent into the reactor under conditions effective to burn off the carbonaceous materials in the reactor. The oxidizing agent, for example, can comprise, but is not limited to, $H_2O$, $CO_2$, $O_2$ (oxygen), air, $O_3$, $Cl_2$, $N_2O$, and combinations of these. This oxidation step can be carried out in pure or diluted oxidizing agent, e.g., oxygen at a temperature range of from about 100° C. to about 700° C., about 200° C. to about 600° C., about 300° C. to about 500° C., or about 400° C. to about 500° C. When a diluted oxidizing agent is used, the dilution can be as high as practically possible, for example, about 0.1% volume of oxidizing agent. In a preferred embodiment, the concentration of oxidizing agent after dilution ranges from about 0.5 to about 21 vol %, preferably from about 1 to about 5 vol %, and more preferably from about 2 to about 3 vol %. In another preferred embodiment, air is used as oxygen source and diluted air is used. In yet another preferred embodiment, air is used together with steam in a steam-air decoking process, in which air is used to burn off the carbonaceous materials and steam is used to keep the burning temperatures low such that they do not exceed the maximum tolerable temperatures. This step may be used independently or in conjunction with any of the alternative methods herein. In certain embodiments, after the impurities are removed using the oxidizing agent, the reactor is then treated with a reducing agent in accordance with the teachings above.

In yet another embodiment, the step of removing impurities from the reactor may be achieved by physically removing carbonaceous materials and metal halides from the reactor. This physical removal step may include, for example, electrical polishing and mechanical polishing. In another example, these impurity deposits can be washed away with high flow rate of water or steam. Again, this step may be used independently or in conjunction with any of the alternative methods herein.

In certain non-limiting embodiments, the specific steps used in the process of removing the impurities may be directed to improve either selectivity or catalyst activity. With respect to improving selectivity and preventing selectivity changeover, for example, the reducing step may be performed for purposes of substantially removing the impurities from the reactor walls. With respect to catalyst activity, it may be recovered or regenerated by oxidation treatment followed by reduction treatment. Alternatively, either selectivity or catalytic activity may be improved by polishing treatment.

The process of the invention may be employed upon the detection of preset or otherwise determined levels of selectivity, for example, upon reaching an undesired selectivity of HFO-1234$_{yf}$ or HCFO-1233$_{xf}$. In one embodiment, the invention is directed to a process for improving the selectivity for 2,3,3,3-tetrafluoropropene where the process is as herein described, comprising: (a) providing a reaction to make 2,3,3,3-tetrafluoropropene, the reaction taking place in a reactor, the reaction having a first selectivity for 2,3,3,3-tetrafluoropropene, which first selectivity, in one embodiment, is at least 90% or higher as herein described; (b) detecting a second selectivity for 2,3,3,3-tetrafluoropropene as the reaction proceeds, for example, the second selectivity is lower than the first selectivity, and includes without limitation undesirable selectivity for commercial purposes, which selectivity in one embodiment is lower than 90%, including about 50% or less; (c) ceasing the reaction; (d) removing impurities from a reactor such that the reactor is substantially free of impurities; removal of impurities in this regard includes removal by (i) introducing a reducing agent, (ii) introducing an oxidizing agent, or (iii) by mechanical removal, or by combinations of (i), (ii) or (iii) as herein described. In one embodiment, removal of impurities is by introducing a reducing agent into the reactor under conditions effective to reduce the impurities; and (e) resuming the reaction after the removal of impurities step. In one embodiment in this regard, the resumed reaction has a third selectivity for 2,3,3,3-tetrafluoropropene that is detected, the third selectivity for 2,3,3,3-tetrafluoropropene being greater than the second selectivity for 2,3,3,3-tetrafluoropropene; in one practice in this regard, the third selectivity for 2,3,3,3-tetrafluoropropene is substantially the same as the first selectivity. In one practice of this embodiment, the process further comprises, after step (c) and prior to introducing the reducing agent, introducing an oxidizing agent into the reactor under conditions effective to oxidize the impurities. In another practice of this embodiment, the process further comprising purging the reactor with an inert gas after the impurities are oxidized and prior to introducing the reducing agent. In another practice of this embodiment, physical removal of impurities, e.g. polishing and hydraulic method and the like, can take place prior to or after reduction and/or prior to or after purging and/or prior to or after oxidation.

The following are examples of the invention and are not to be construed as limiting.

EXAMPLES

Example 1

Figure 2:
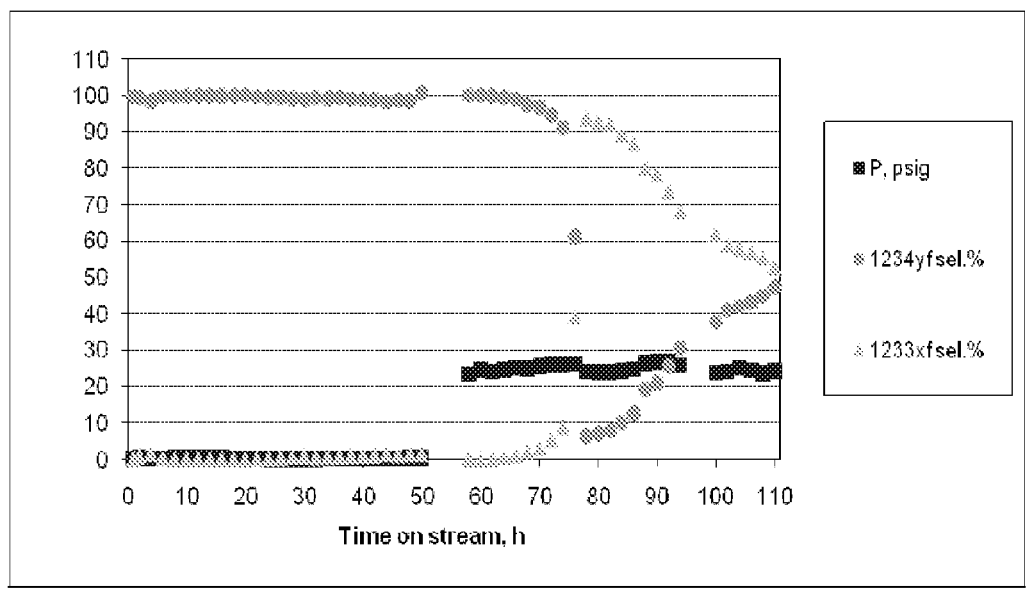
FIG. 2 illustrates conversion of HCFC-244bb during dehydrochlorination in ¾" Inconel 625×0.035" reactor (450° C., 12 g-organic/h, organic feed: 99.4 GC area % 244bb/0.4% 1233xf GC area %).

This example illustrates the occurrence of selectivity changeover from HFO-1234yf to HCFO-1233xf during vapor phase dehydrochlorination reaction of HCFC-244bb. A cylindrical Inconel 625 reactor of ¾" diameter immersed into a 3-zone electrical furnace was used. Process temperatures were recorded using a multi-point thermocouple placed inside the reactor. The inner wall of Inconel 625 reactor serves as dehydrochlorination catalyst. A feed containing 99.4 GC area % HCFC-244bb and 0.4 GC area % HCFO-1233xf was fed into the bottom of the vertically mounted reactor and was vaporized before reaching reaction zone. The reaction was conducted under conditions of 450° C., 0 and 25 psig, and 12 g-organic/h. Effluent gases were passed through a gas sampling tube so that the progress of the reaction was monitored periodically via GC analysis of the contents of the gas sampling tube. As shown in FIG. 1 and FIG. 2, after about 20 hours on stream at 450° C. and about 25 psig, HCFC-244bb conversion was dramatically increased from about 30% initially to almost 100% while HFO-1234yf selectivity was dramatically decreased from about 99.5% initially to below 10% (simultaneously, HCFO-1233xf selectivity was increased from below 0.5% to above 90%), indicating the occurrence of selectivity changeover from HFO-1234yf to HCFO-1233xf. After that, even though the selectivity to HCFO-1233xf started to drop, it remained at about 50% at the end of the experiment.

Example 2

Figure 3:
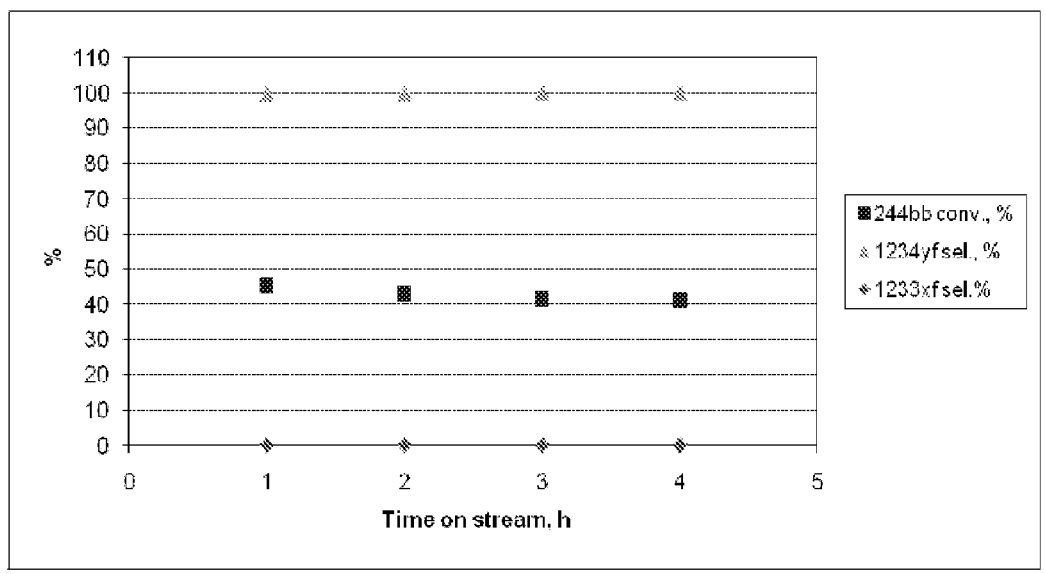
FIG. 3 illustrates conversion of HCFC-244bb and product selectivity during HCFC-244bb dehydrochlorination in reduced ¾" Inconel 625×0.035" reactor (480° C., 0 psig, 12 g-organic/h, organic feed: 99.4 GC area % 244bb/0.4% 1233xf GC area %).

This example is a continuation of Example 1. After the occurrence of selectivity changeover from HFO-1234yf to HCFO-1233xf, the reactor was reduced in hydrogen flow (200 ml/min) for 2 hours at 480° C. and then the reaction of HCFC-244bb dehydrochlorination was re-started. As shown in FIG. 3, the selectivity to HFO-1234yf was almost 100% and the conversion of HCFC-244 was above 40% after reduction treatment.

What is claimed is:

1. A process for preparing 2,3,3,3-tetrafluoropropene comprising:
   (a) removing impurities selected from the grow consisting of metal halides, metal oxides, and carbonaceous materials from a reactor such that the reactor is substantially free of impurities;
   (b) providing a starting composition comprising 2-chloro-1,1,1,2-tetrafluoropropane in the reactor under conditions effective to produce a final composition comprising 2,3,3,3-tetrafluoropropene.

2. The process of claim 1, wherein the metal halides comprise halides of Ni, Cr, Fe, Mo, Nb, Cu, and Co.

3. The process of claim 1, wherein the step of removing impurities from the reactor comprises introducing a reducing agent into the reactor under conditions effective to convert any metal halides or metal oxides into metallic metals.

4. The process of claim 3, wherein the reducing agent is selected from the group consisting of $H_2$, $NH_3$, CO, $C_1$-$C_{12}$ hydrocarbons, and combinations of these.

5. The process of claim 1, wherein the step of removing impurities from the reactor comprises introducing an oxidizing agent into the reactor under conditions effective to burn off the carbonaceous materials in the reactor.

6. The process of claim 5, wherein the oxidizing agent is selected from the group consisting of $H_2O$, $CO_2$, $O_2$, air, $O_3$, $Cl_2$, $N_2O$, and combinations of these.

7. The process of claim 6, wherein the oxidizing agent comprises oxygen.

8. The process of claim 1, wherein the step of removing impurities from the reactor comprises physically removing carbonaceous materials, metal oxides, and metal halides from the reactor.

9. The process of claim 8, wherein the step of physically removing the carbonaceous materials, metal oxides, and metal halides from the reactor is selected from the group consisting of electrical polishing, mechanical polishing, hydraulic methods, and combinations of these.

10. The process of claim 1, wherein the selectivity to 2,3,3-tetrafluoropropene is at least 90% or higher.

11. A process for preparing 2,3,3,3-tetrafluoropropene comprising:
(a) providing a starting composition including a compound of Formulae I, II, or III:

$$CX_2=CCl-CH_2X \qquad (I);$$

$$CX_3-CCl=CH_2 \qquad (II); or$$

$$CX_3-CHCl-CH_2X \qquad (III)$$

wherein X is independently selected from F, Cl, Br, and I, provided that at least one X is not fluorine;
(b) contacting the starting composition with a first fluorinating agent to produce a first intermediate composition including 2-chloro-3,3,3-trifluoropropene;
(c) contacting the first intermediate composition with a second fluorinating agent to produce a second intermediate composition comprising 2-chloro-1,1,1,2-tetrafluoropropane;
(d) dehydrochlorinating at least a portion of the 2-chloro-1,1,1,2-tetrafluoropropane to produce a reaction product comprising 2,3,3,3-tetrafluoropropene, wherein the dehydrochlorinating step is provided in a reactor that is substantially free from impurities.

12. A process for preparing 2,3,3,3-tetrafluoropropene comprising:
(a) providing a reaction to make 2,3,3,3-tetrafluoropropene, the reaction taking place in a reactor, the reaction having a first selectivity for 2,3,3,3-tetrafluoropropene;
(b) detecting a second selectivity for 2,3,3,3-tetrafluoropropene as the reaction proceeds;
(c) ceasing the reaction;
(d) removing impurities from a reactor such that the reactor is substantially free of impurities by introducing a reducing agent into the reactor under conditions effective to reduce the impurities; and
(e) resuming the reaction.

13. The process of claim 12 further comprising, after step (c) and prior to introducing the reducing agent, introducing an oxidizing agent into the reactor under conditions effective to oxidize the impurities.

14. The process of claim 13 further comprising purging the reactor with an inert gas after the impurities are oxidized and prior to introducing the reducing agent.

15. The process of claim 12 wherein the resumed reaction has a third selectivity for 2,3,3,3-tetrafluoropropene, the third selectivity for 2,3,3,3-tetrafluoropropene being greater than the second selectivity for 2,3,3,3-tetrafluoropropene.

16. The process of claim 12 wherein the oxidizing agent is selected from the group consisting of $H_2O$, $CO_2$, $O_2$, air, $O_3$, $Cl_2$, $N_2O$ and combinations of these.

17. The process of claim 12 wherein the reducing agent is selected from the group consisting of $H_2$, $NH_3$, CO, $C_1$-$C_{12}$ hydrocarbons, and combinations of these.

\* \* \* \* \*